(12) United States Patent
Kim et al.

(10) Patent No.: US 6,183,992 B1
(45) Date of Patent: Feb. 6, 2001

(54) METHOD FOR MASS PRODUCTION OF ANTIMICROBIAL PEPTIDE

(75) Inventors: Sun-Chang Kim; Jae Hyun Lee, both of Taejon; Min Hyung Kang, Seoul; Jeong Hyun Kim; Seung-Suh Hong, both of Taejon; Hyun-Soo Lee, Seoul, all of (KR)

(73) Assignees: Samyang Genex Corporation; Korea Advanced Institute of Science and Technology, both of Taejon (KR)

( * ) Notice: Under 35 U.S.C. 154(b), the term of this patent shall be extended for 0 days.

(21) Appl. No.: 09/230,180

(22) PCT Filed: May 28, 1998

(86) PCT No.: PCT/KR98/00132

§ 371 Date: Mar. 10, 1999

§ 102(e) Date: Mar. 10, 1999

(87) PCT Pub. No.: WO98/54336

PCT Pub. Date: Dec. 3, 1998

(30) Foreign Application Priority Data

May 28, 1997 (KR) ................................. 97/21312
Apr. 9, 1998 (KR) ................................. 98/13372

(51) Int. Cl.[7] ........................................... C12P 21/06
(52) U.S. Cl. ............................................... 435/69.7
(58) Field of Search ............................................ 435/69.7

(56) References Cited

U.S. PATENT DOCUMENTS 5,593,866    1/1997    Hancock et al. ................... 435/69.7

*Primary Examiner*—Karen Cochrane Carlson
(74) *Attorney, Agent, or Firm*—Darby & Darby PC

(57) ABSTRACT

The present invention provides a method for mass production of an antimicrobial peptide, which comprises the steps of: constructing a fusion gene containing a first gene encoding a negatively charged acidic peptide having at least two cysteine residues and a second gene encoding a positively charged basic antimicrobial peptide; transforming a host microorganism with an expression vector comprising the fusion gene; cultivating the transformed microorganism to express a fusion peptide containing the acidic peptide and antimicrobial peptide, and, recovering the expressed antimicrobial peptide. In accordance with the present invention, the inhibitory effect of the expressed antimicrobial peptide on the growth of the host microorganism can be dramatically minimized by fusing it with the acidic peptide. Accordingly, antimicrobial peptides can be produced massively from a recombinant microorganism regardless of the kind of the antimicrobial peptides.

5 Claims, 10 Drawing Sheets

FIG. 1A

```
5' CCC CCC GTC GAC GAG AAT GCG GAG GAC ACA
   Pro Pro Val Asp Glu Asn Ala Glu Asp Thr

CAT GGT CTC TGC GGG GAA AAA ACC TGC TCT
   His Gly Leu Cys Gly Glu Lys Thr Cys Ser

CCA GCA CAA GTC TGT CTA AAC AAC GAA TGC
   Pro Ala Gln Val Cys Leu Asn Asn Glu Cys

GTT TGC ACT GCA ATC AGA TGC GAG ATC TTC
   Val Cys Thr Ala Ile Agr Cys Glu Ile Phe

TGT CCT AAC GGA TTC AAA GTT GAT GAG AAT
   Cys Pro Asn Gly Phe Lys Val Asp Glu Asn

GGA TGC GAA TAC CCA TGT ACC TGC GCG GGG ATC 3'
   Gly Cys Glu Tyr Pro Cys Thr Cys Ala Gly Ile
```

FIG. 1B

```
5' CCC CTG TGC GAT GCA GAA GCA GTA GGA CCA
   Pro Leu Cys Asp Ala Glu Ala Val Gly Pro

GAG GCC TTT GCA GAT GAA GAT TTA GAT GAA TGC 3'
   Glu Ala Phe Ala Asp Glu Aps Leu Asp Glu Cys
```

METHOD FOR MASS PRODUCTION OF ANTIMICROBIAL PEPTIDE

BACKGROUND OF THE INVENTION

1. Field of the Invention

The present invention relates to a method for mass production of an antimicrobial peptide, more specifically, to a method for mass production of an antimicrobial peptide by producing the antimicrobial peptide in a form of fusion protein with a foreign peptide through gene manipulation.

2. Description of the Prior Art

In general, antimicrobial peptides do not easily lose their biological activities by physical and chemical factors such as heat, alkali, etc. Moreover, they do not readily induce a resistance to microorganisms as they show an antimicrobial activity through their characteristic action mechanism which is clearly discriminated from conventional antibiotics. Thus, antimicrobial peptides have enjoyed high industrial applicability in the areas of pharmacy, food, etc.

However, there is a crucial problem in the industrial application of the antimicrobial peptides, since the conventional techniques do not permit mass production of the peptides at a low price. For example, chemical synthesis does not allow the mass production of the antimicrobial peptides in an economical manner. In this regard, genetic engineering technology employing recombinant microorganisms, has been suggested in the art as an alternative means. However, it has also revealed a disadvantage of low productivity since the expressed antimicrobial peptides inhibit the growth of the recombinant microorganisms.

U.S. Pat. No. 5,205,154 discloses a gene construct comprising a gene of a carrier polypeptide inhibiting the antimicrobial activity of cecropin and a gene of cecropin, where araB is employed as the carrier polypeptide, though the nature of the carrier polypeptide is not critical.

U.S. Pat. No. 5,593,866 teaches a process for preparing a positively charged antimicrobial peptide as a fusion protein with a negatively charged peptide to inhibit bacterial proteolysis, where glutathione-S-transferase, protein A, IgG-binding domain of protein A, protein F from *Pseudomonas aeruginosa* or prepro defensin is employed as the negatively charged peptide.

Accordingly, there are strong reasons for exploring and developing alternative means for mass production of the antimicrobial peptide in an economical manner.

SUMMARY OF THE INVENTION

The present inventors have made an effort to solve the disadvantages of low productivity and poor economy in the course of manufacturing the antimicrobial peptide, and successfully prepared the antimicrobial peptide in a massive and economical manner by the aid of recombinant DNA technology.

A primary object of the present invention is to provide a method for mass production of an antimicrobial peptide in recombinant microorganisms, which employs an expression system permitting mass production of the antimicrobial peptide.

BRIEF DESCRIPTION OF THE DRAWINGS

The above and the other objects and features of the present invention will become apparent from the following descriptions given in conjunction with the accompanying drawings, in which:

FIG. 1(A) shows a nucleotide sequence (SEQ ID NO:1) of Guamerin gene and amino acid sequence translated therefrom (SEQ ID NO:2).

FIG. 1(B) shows a nucleotide sequence (SEQ ID NO:3) of MMIS(modified magainin intervening segment) gene and amino acid sequence translated therefrom (SEQ ID NO:4).

DETAILED DESCRIPTION OF THE INVENTION

Figure 2A:
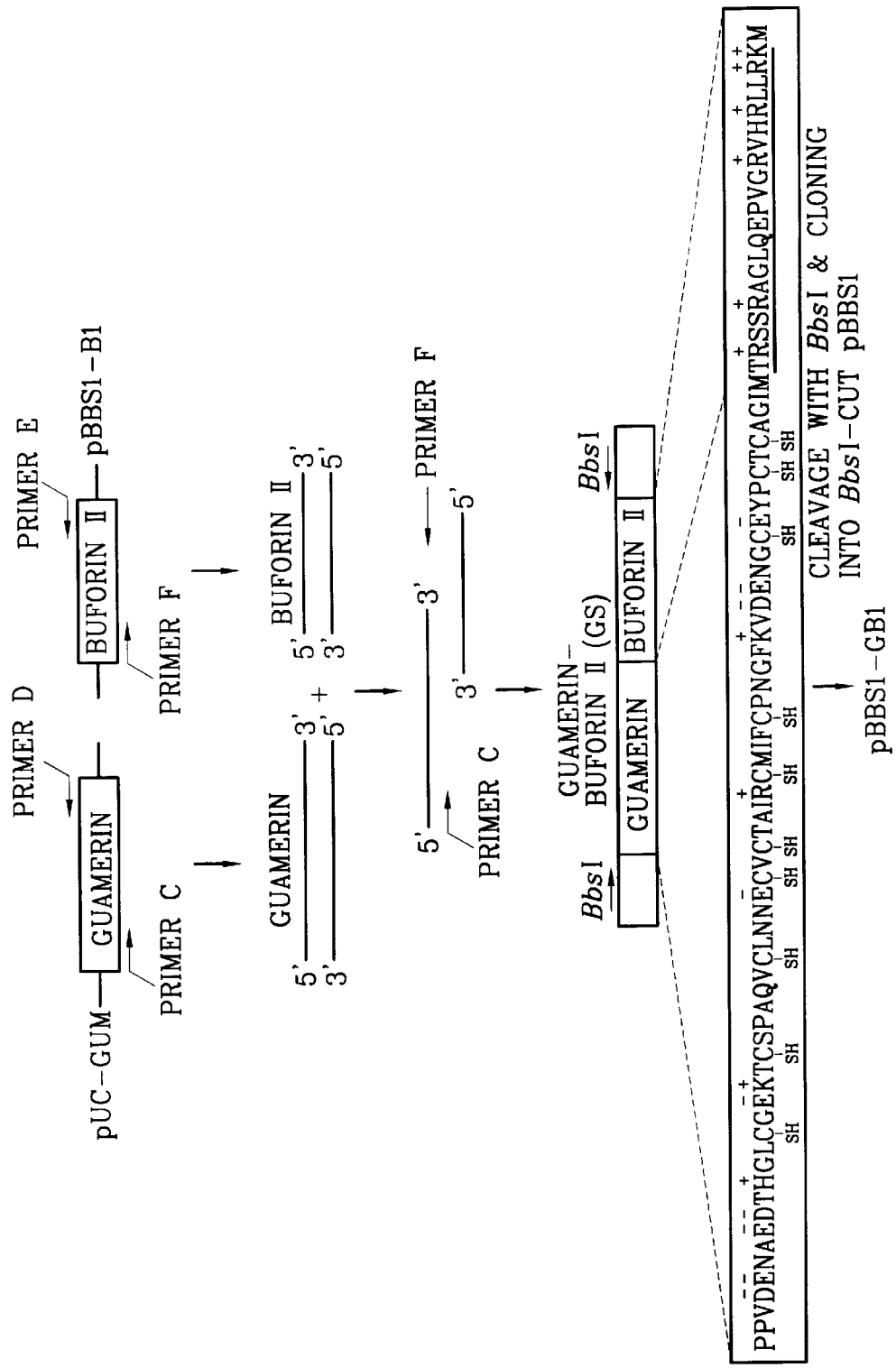
FIG. 2(A) is a schematic diagram showing a construction strategy of a fusion product (SEQ ID NO:5) of a Guamerin gene with a Buforin II gene by PCR.

A method for mass production of an antimicrobial peptide of the present invention, comprises the steps of: constructing a fusion gene containing a first gene encoding an acidic peptide having at least two cysteine residues and a second gene encoding a basic antimicrobial peptide; transforming a host microorganism with an expression vector comprising the fusion gene; culturing the transformed microorganism to express a fusion peptide containing the acid peptide and the antimicrobial peptide; and, recovering the antimicrobial peptide from the fusion peptide.

In carrying out the present invention, a gene construct which comprises a first gene encoding an acidic peptide having at least two cysteine residues and a second gene encoding a basic antimicrobial peptide, and an expression vector which comprises a promoter operably linked to a gene sequence containing a first gene encoding an acidic peptide having at least two cysteine residues and a second gene encoding a basic antimicrobial peptide, are essentially required, and the fusion gene may be present in a form of monomer or multimer.

Contrary to the results in U.S. Pat. No. 5,593,866, the present inventors discovered that: a general acidic peptide gene does not permit an efficient expression of a basic antimicrobial peptide; and, the presence of at least two cysteine residues in the acidic peptide can efficiently solve the said problem.

In the gene construct of the invention, a first gene codes for an acidic peptide having at least two cysteine residues and neutralizing positive charges of an antimicrobial peptide substantially. Although the length of the acidic peptide is not limited, it is, preferably, equal to or longer than that of the antimicrobial peptide in order to efficiently neutralize the charges of a desired antimicrobial peptide, when considering length and distribution of positive charges. Furthermore, the acidic peptide has two or more cysteine residues. It is postulated that the cysteine residues promote interaction between negative charges of the acidic peptide and positive charges of the antimicrobial peptide by the formation of a secondary structure through disulfide bonds.

In accordance with the present invention, the acidic peptide may be synthesized artificially or selected among natural acidic peptides, and may be obtained using the synthetic gene encoding the peptide or isolated from nature. The artificially designed acidic peptide has two or more cysteine residues, and the natural acidic peptide may be modified to have sufficient cysteine residues. Also, the acidic peptide gene may be modified in various ways for the purpose of easy fusion with a second gene encoding the antimicrobial peptide, easy isolation of the antimicrobial peptide from the fusion peptide, or the preparation of various multimeric forms of a fusion gene.

For example, the acidic peptide gene may be synthesized or modified so that it can be connected to the antimicrobial peptide gene to have a correct reading frame resulting the desired antimicrobial peptide. Also, the acidic peptide gene may be synthesized or modified to include nucleotide sequences encoding a cleavage site for a specific protease or a chemical in order to isolate the antimicrobial peptide from the expressed fusion peptide.

The acidic peptide gene may be selected to have the most suitable length for the neutralization of the antimicrobial peptide among monomers or multimers of the acidic peptide genes. The multimer of an acidic peptide gene may be prepared by employing gene amplification technique. For example, vectors comprising multimers of an acidic peptide gene can be prepared by inserting an acidic peptide gene between two Class-IIS restriction enzyme sites of a vector containing two oppositely oriented Class-IIS restriction enzyme sites, digesting the vector with a Class-IIS restriction enzyme, isolating a DNA fragment containing the acidic peptide gene, self-ligating the isolated DNA fragments to prepare multimers, and cloning the various multimers into the vector digested with the Class-IIS restriction enzyme (see: Lee, J. H. et al., Genetic Analysis: Biomolecular Engineering, 13:139–145(1996)).

In accordance with the present invention, the antimicrobial peptide may be designed artificially or selected among natural acidic peptides, and may be obtained using the synthetic gene encoding the desired peptide or isolated from nature. The antimicrobial peptide gene may be modified in various ways for the purpose of easy fusion with the acidic peptide gene, easy isolation of the antimicrobial peptide from the fusion peptide, or the preparation of various multimeric forms of the fusion gene.

For example, the antimicrobial peptide gene may be modified so that the C-terminal region of the antimicrobial peptide can be connected to the N-terminal region of the acidic peptide in a correct reading frame (antimicrobial peptide gene I).

Also, the antimicrobial peptide gene may be modified to include nucleotide sequences encoding a site cleaved by a specific protease or a chemical at the N-terminus in order to isolate the antimicrobial peptide from the expressed fusion peptide, and nucleotide sequences permitting termination of peptide synthesis at the C-terminus of the antimicrobial peptide (antimicrobial peptide gene II).

In addition, the antimicrobial peptide gene may be modified to include nucleotide sequences encoding a cleavage site for a specific protease or a chemical (for example, a codon encoding a methionine residue for the cleavage by CNBr) at the N-terminus and the C-terminus of the antimicrobial peptide in order to isolate the antimicrobial peptide from the expressed fusion peptide (antimicrobial peptide gene III).

The fusion gene may be prepared by ligating the acidic peptide gene and the antimicrobial peptide gene prepared as described above, and the acidic peptide gene or the antimicrobial peptide gene may be a monomer or a multimer as mentioned above.

In accordance with the present invention, the fusion gene contains a first gene encoding an acidic peptide and a second gene encoding an antimicrobial peptide gene, and those may be ligated directly or indirectly through linker, etc., if the two genes are connected in a correct reading frame.

In a preferred embodiment of the invention, the fusion gene may be prepared by modifying the acidic peptide gene and the antimicrobial peptide gene to have complementary nucleotide sequences at the 3'-termini of single strands of each gene, annealing two genes via a partial hybridization, and performing PCR with the hybridized genes as a template and with primers corresponding to the sequences to the 5'-termini of respective single stranded genes.

Various number of monomer of a fusion gene thus prepared, may be concatenated to prepare various multimers of the fusion gene by the conventional methods in the art, e.g., self-ligation of a fusion gene. A multimer of a fusion gene may be also prepared by employing gene amplification system. For example, vectors containing multimers of a fusion gene can be prepared by inserting the fusion gene between two Class-IIS restriction enzyme sites of a vector containing two oppositely oriented Class-IIS restriction enzyme sites, digesting the vector with the Class-IIS restriction enzyme, isolating a DNA fragment containing the fusion gene, self-ligating the isolated DNA fragments to prepare multimers of a fusion gene, and cloning the multimers of the fusion gene into the vector digested with the Class-IIS restriction enzyme.

In a preferred embodiment of the invention, a multimer of a fusion gene is a multimer of the fusion gene comprising antimicrobial peptide gene III.

In a preferred embodiment of the invention, a multimer of a fusion gene is a multimer wherein the fusion gene comprising antimicrobial peptide gene II is ligated to 3'-terminus of a monomer or multimer of a fusion gene comprising antimicrobial peptide gene I.

In a preferred embodiment of the invention, a multimer of a fusion gene is a multimer wherein the fusion gene comprising antimicrobial peptide gene II is ligated to 3'-terminus of a monomer or multimer of a fusion gene comprising antimicrobial peptide gene III.

A multimer of a fusion gene can be cloned into a suitable expression vector and expressed in a microorganism, e.g., E. coli, to express multimer of the fusion peptide. The multimer of the fusion peptide is treated with an enzyme or a chemical, e.g., CNBr, to remove the acidic peptide and separate the antimicrobial peptide into monomers, and the antimicrobial peptide is purified using cation-exchange chromatography, etc. When a multimer of a fusion peptide obtained after expression of a multimer is treated with an enzyme or a chemical, e.g., CNBr, the antimicrobial peptide present at the end of the multimer may be obtained in a monomer of native form.

The present invention is further illustrated in the following examples, which should not be taken to limit the scope of the invention. Particularly, since antimicrobial peptides, acidic peptides and genes of their multimers used in Examples are only preferred embodiments of the invention, the present invention covers all of the inventions employing an acidic peptide containing at least two cysteins residues for the purpose of mass production of various basic antimicrobial peptides.

EXAMPLE 1

Selection of Acidic Peptides

The native Guamerin (hereinafter, referred to as "G"; Jung, H. I. et al.(1995) J. Biol. Chem., 270:13879–13884) and a modified MIS (hereinafter, referred to as "M"; Zasloff, M.(1987) Proc. Natl. Acad. Sci., USA, 84:5449–5453) which have a lot of cysteine residues were employed as acidic peptides. As can be seen in FIGS. 1(A) and 1(B) (wherein only sense sequences were shown), single stranded oligonucleotides (SEQ ID NO:1; and, SEQ ID NO:3) encoding the acidic peptides were synthesized.

The oligonucleotides thus synthesized were dissolved in TE buffer (pH 8.0) in the same molar ratio, heated at 70° C. for 10 minutes, and left to stand at 0° C. for 30 minutes. After 20% (w/v) polyacrylamide gel electrophoresis, double stranded DNA fragments were isolated, and cloned into pBBS1 vector (see: Lee, J. H. et al., Genetic Analysis: Biomolecular Engineering, 13:139–145(1996)) digested with BbsI to construct pBBS1-$G_1$ (Guamerin) or pBBS1-$M_1$ (MIS) vector. Since, multimers (pBBS1-$G_n$ or pBBS1-$M_n$, n=1,2,3, . . . ) of the acidic peptide genes can be prepared using the pBBS1-$G_1$, or pBBS1-$M_1$ vector thus constructed, the acidic peptides having the most suitable length to neutralize an antimicrobial peptide were selected.

EXAMPLE 2

Preparation of an Antimicrobial Peptide Gene

In order to prepare an antimicrobial peptide by expressing the antimicrobial peptide in a multimeric form of a fusion peptide and treating it with CNBr, methionine codons were introduced to both ends of a gene of Buforin II(TRSSRAGLQFPVGRVHRLLRK(SEQ ID NO:9); Park, C. B. et al., (1996) Biochem. Biophys. Res. Comm., 218, 408–413), an antimicrobial peptide.

A DNA sequence encoding Buforin II (hereinafter, referred to as "B") was synthesized and cloned into pBBS1 vector digested with BbsI to construct pBBS1-B1 vector. The resulting pBBS1-B1vector contains a complete Buforin II gene and two methionine codons at both ends of the Buforin II gene.

EXAMPLE 3

Figure 2B:
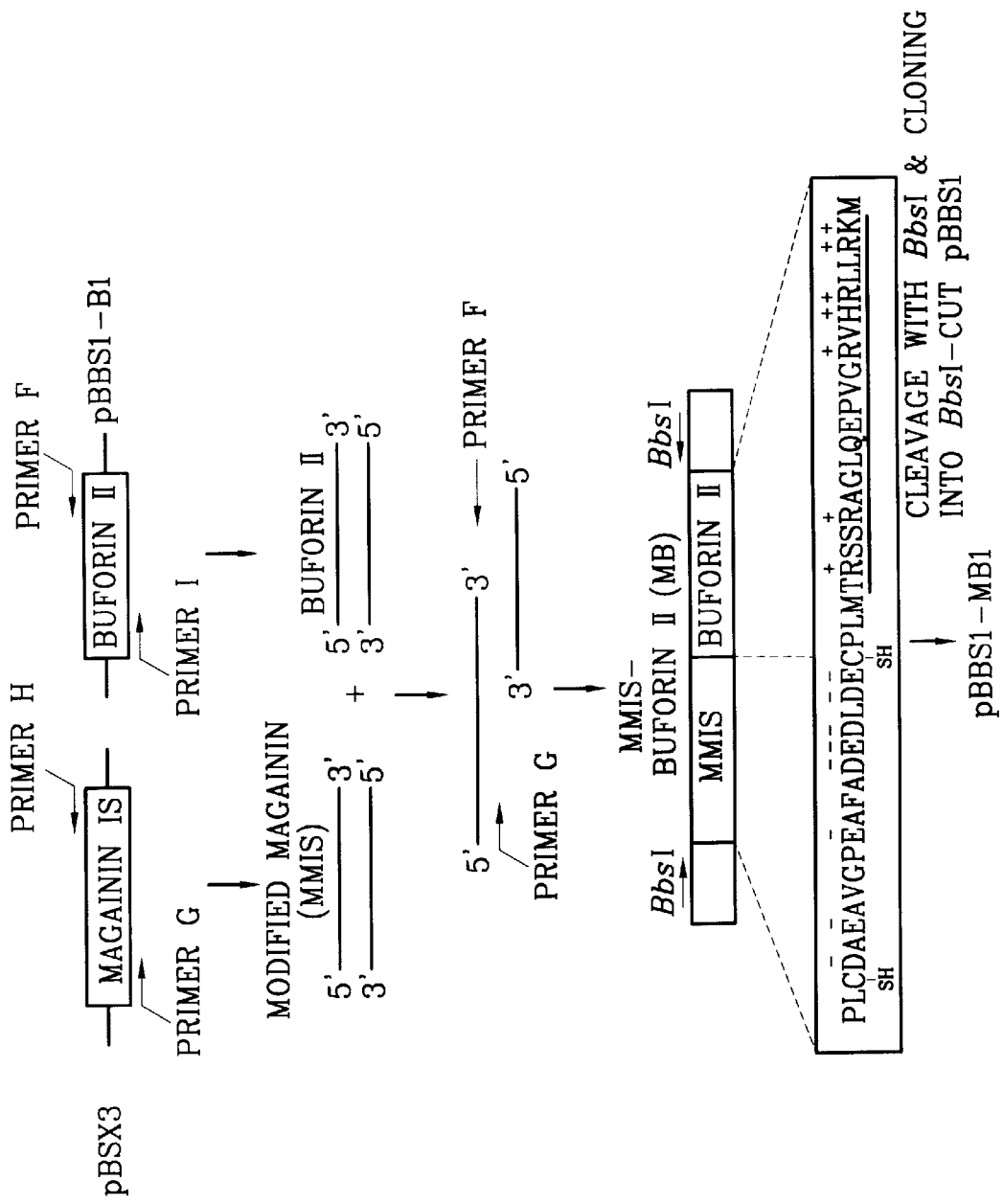
FIG. 2(B) is a schematic diagram showing a construction strategy of fusion product (SEQ ID NO:6) of a MMIS gene with a Buforin II gene by PCR.

Preparation of a Fusion Gene Containing an Acidic Peptide Gene and an Antimicrobial Peptide Gene In order to prepare a fusion gene containing the acidic peptide gene and the antimicrobial peptide gene obtained in Examples 1 and 2, PCR was carried out as followings (see: FIGS. 2(A) and 2(B)): Using a couple of primers corresponding to 5'-end and 3'-end of the acidic peptide (i.e., Guamerin) gene (primer 1:5'-AAAGAAGACGGCCCCCGGTCGACGAGAATGCG-3' (SEQ ID NO:10) and primer 2:5'-GCTGCTACGGGTCATGATCCCCGCGCAGGT-3'(SEQ ID NO:11)), respectively, the Guamerin gene was amplified by the aid of PCR technique. On the other hand, using a couple of primers corresponding to 5'-end and 3'-end of the antimicrobial peptide (Buforin II) (primer 3:5'-ACCTGCGCGGGGATCATGACCCGTAGCAGC-3'(SEQ ID NO:12) and primer 4:5'-TGCATGCCTGCAGGTCGA-3'(SEQ ID NO:13), respectively, the Buforin II gene was amplified by PCR.

The PCR products thus amplified were mixed in a same molar ratio and amplified again by PCR using primer 1 (SEQ ID NO:10) and primer 4 (SEQ ID NO:13). The PCR product thus obtained was digested with BbsI. Then, the fragments of the fusion gene containing the Guamerin gene and the Buforin II gene were isolated and cloned into pBBS1 vector digested with BbsI to construct pBBS1-(GB)1 vector (see: FIG. 2(A)).

Figure 3:
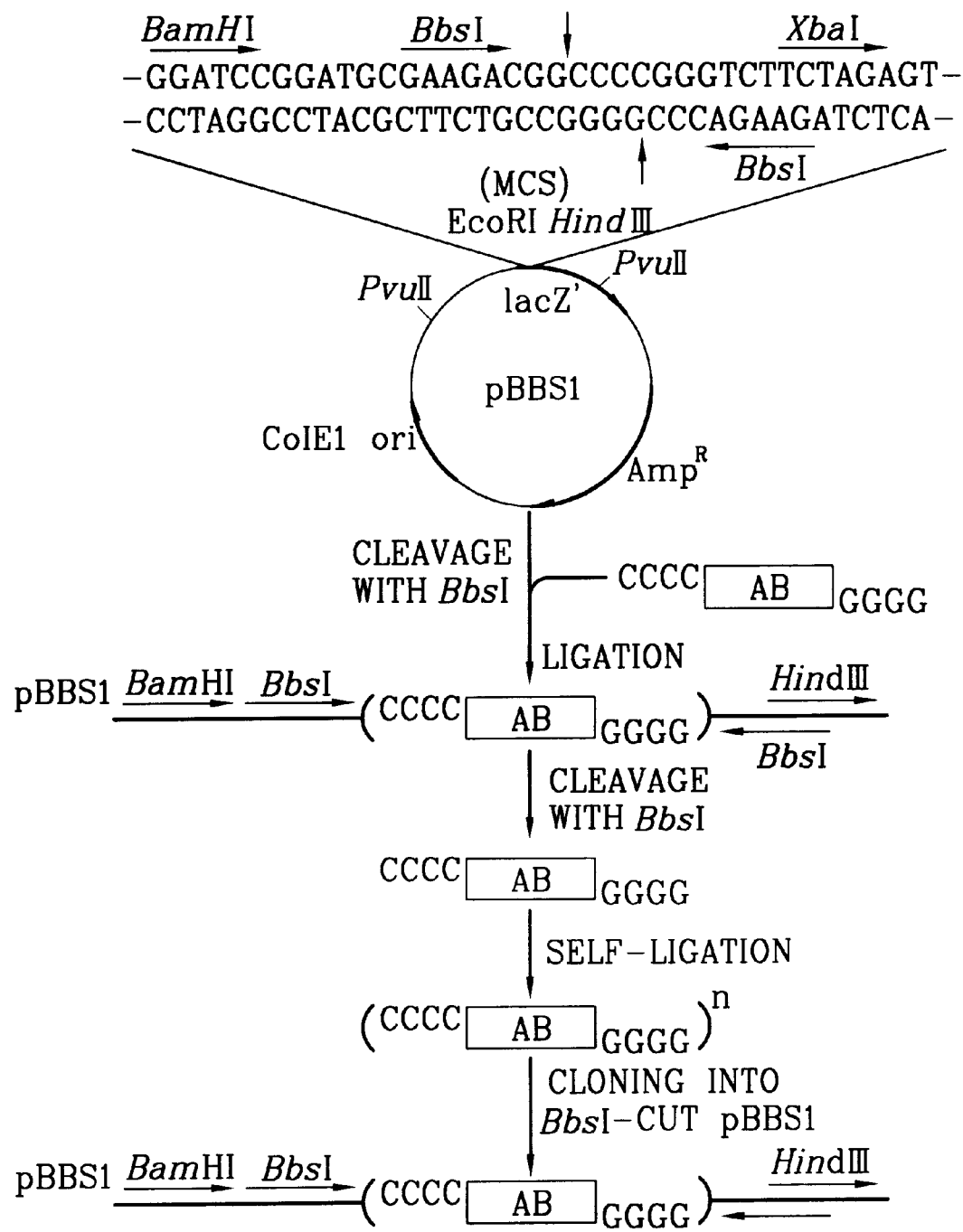
FIG. 3 is a schematic diagram showing a construction strategy of a multimeric fusion gene using a gene amplification vector.

And then, in order to prepare multimers of the fusion gene employing gene amplification system, the pBBS1-(GB)1 vector was digested with BbsI and the fragments containing the fusion gene were isolated. The isolated DNA fragments were self-ligated to prepare multimers, and the various multimers were cloned into pBBS1 vector digested with BbsI to construct vectors comprising multimers of the fusion gene which were designated as pBBS1-$(GB)_n$(n=1,2,3, 4, . . . ) (see: FIG. 3).

On the other hand, pBBS1-(MB)1 vector and vectors comprising multimers of the fusion gene, pBBS1-$(MB)_n$(n= 1,2,3,4, . . . ) were constructed in the same manner as mentioned above, except for employing MIS (containing S—S bond) as acidic peptide instead of Guamerin (see: FIG. 2(B)).

EXAMPLE 4

Preparation of a Fusion Gene for the Expression of a Native Antimicrobial Peptide and its Multimers The antimicrobial peptide obtained from the multimers of fusion gene prepared in Example 3 has a homoserine residue at their C-terminus. In order to prepare a native antimicrobial peptide which does not contain the homoserine residue, a fusion gene whose sequence was slightly modified from that of the fusion gene prepared in Example 3 and its multimers were prepared as followings: For this purpose, Guamerin was used as the acidic peptide and MSI-78 (GIGKFLKKAKKFGKAFVKILKK-$NH_2$: SEQ ID NO:14) was used as the antimicrobial peptide, respectively.

Two kinds of antimicrobial peptide genes (hereinafter, referred to as "BI" and "BII", respectively) suitable for the purpose were prepared, where antimicrobial peptide gene I was prepared so that the peptide encoded by this gene may have no methionine residue at the N-terminus, and the C-terminus can be in-frame fused to the following acidic peptide gene in a correct reading frame, and antimicrobial peptide gene II was prepared so that the peptide encoded by this gene may have one methionine residue at N-terminus and peptide synthesis may be terminated at C-terminus.

Figure 4A:
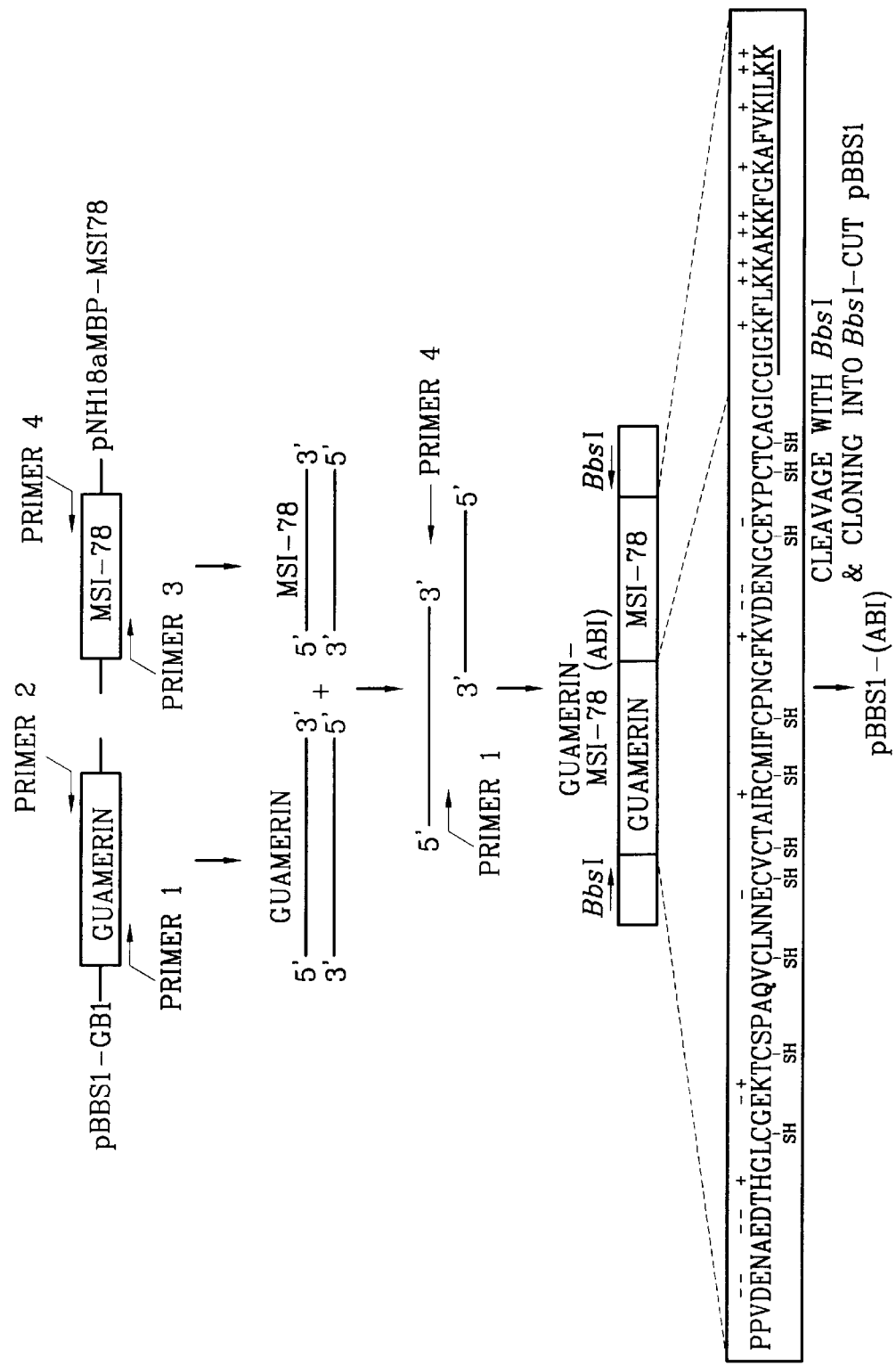
FIG. 4(A) is a schematic diagram showing a construction strategy of a fusion gene (gene I) (SEQ ID NO:7) containing a gene of an antimicrobial peptide MSI-78 and a gene of Guamerin.
Figure 4B:
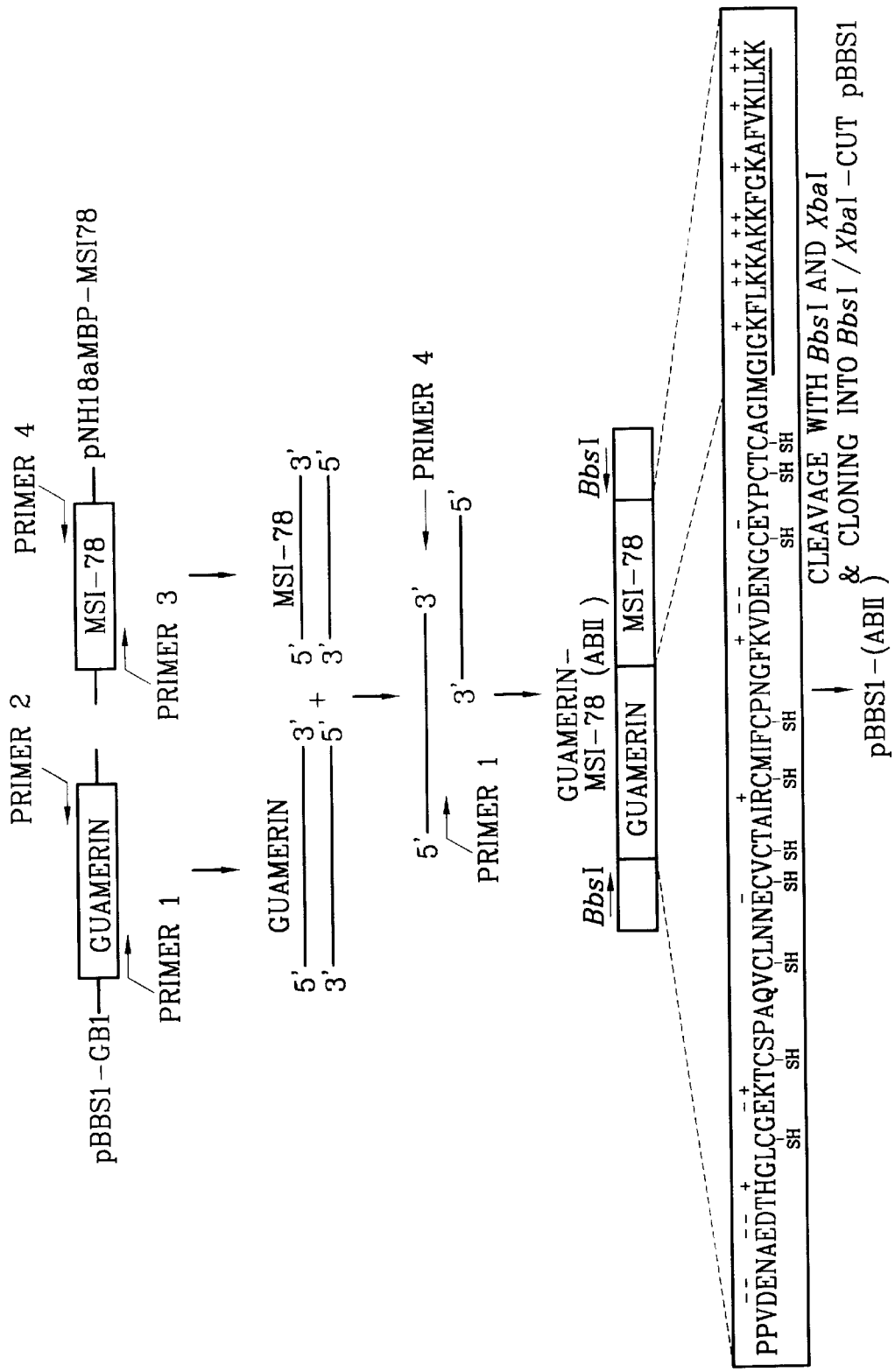
FIG. 4(B) is a schematic diagram showing a construction strategy of a fusion gene (gene II)(SEQ ID NO:8) containing a gene of an antimicrobial peptide MSI-78 and a gene of Guamerin.

The antimicrobial peptide genes I and II thus prepared were ligated with an acidic peptide gene, respectively, in the same manner as in Example 3 to prepare fusion genes, and cloned into pBBS1 vector digested with BbsI to construct pBBS1-$(GBI)_1$ and pBBS1-$(GB\ II)_1$ vectors, respectively (see: FIGS. 4(A) and 4(B)). Multimers of the GB I fusion gene were prepared from the pBBS1-(GB I)$_1$ vector employing gene amplification system, and monomer of the GB II fusion gene was ligated to the ends of the multimers to construct vectors which were designated as pBBS1-[(GB I)$_n$(GB II)] (n=0,1,2,3,4, . . . )

EXAMPLE 5

Expression and Preparation of Antimicrobial Peptide

Figure 5A:
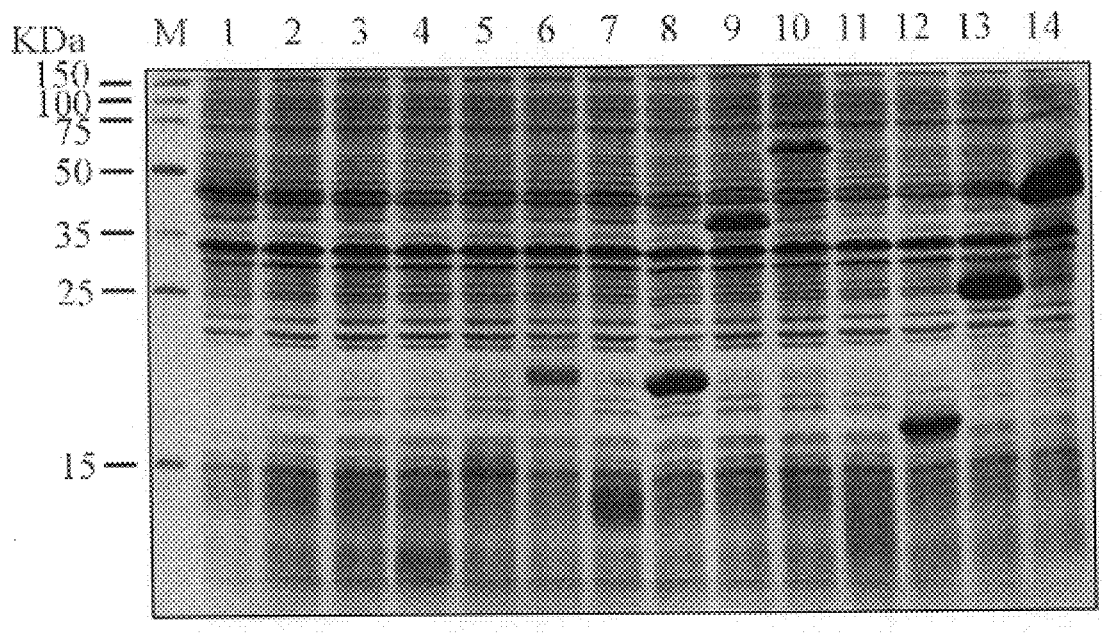
FIG. 5(A) is SDS-PAGE pattern of cell lysates of *E. coli* transformed with vectors containing multimeric fusion gene comprising Guamerin or MMIS after induction of protein expression.

In order to express the multimers of the fusion genes cloned in the vectors prepared in Examples 3 and 4 in *E. coli*, the multimers were cloned into an expression vector pET21c (Novagen, USA) digested with BamHI/HindIII, and transformed into *E. coli* BL21(DE3) to express multimers of the fusion peptides. After the induction of expression of the multimers, the cells were harvested from the cultured media. The lysates thus obtained were analyzed by SDS-PAGE (see: FIG. 5(A)). In FIG. 5(A), lane M shows molecular weight marker; lane 1 shows cell lysates of *E. coli* which does not contain the expression vector; and, lanes 2 to 14 show cell lysates of *E. coli* transformed with pET21c, pET21c-$B_1$, pET21c-$B_2$, pET21c-$B_4$, pET21c-$B_6$, pET21c-$(GB)_1$, pET21c-$(GB)2$, pET21c-$(GB)_4$, pET21c-$(GB)_6$, pET21c-$(MB)_1$, pET21c-$(MB)2$, pET21c-$(MB)_4$, and pET21c-$(MB)_6$, respectively. As shown in FIG. 5(A), it was found that the expression of the multimers remarkably increased compared to that of the multimers of Buforin II alone. Among the recombinant *E. coli* containing an expression vector, one recombinant showing maximum expression was finally selected.

Inclusion bodies of the multimer of the fusion peptide whose expression was confirmed as above were suspended in a solution containing 1N HCl and 6M guanidinium chloride, and treated with 1M CNBr. Then, the peptides were collected by reverse-phase concentration using Sep-Pak, and the antimicrobial peptides with positive charges were purified by QAE-Sephadex (Sigma Chemical Co., USA) anion-exchange chromatography. The antimicrobial peptide thus isolated was further purified by reverse-phase HPLC to obtain a pure recombinant antimicrobial peptide. The analysis of biological activity of the purified recombinant antimicrobial peptide has revealed that it has the same antimicrobial activity as that of the native one.

Comparative Example 1

A gene encoding prepromagainin (SEQ ID NO:15) which has a similar structure to $(MB)_6$ but contains no cysteine residue, was cloned into a pET21b (Novagen, USA) vector and transformed into *E. coli* BL21(DE3). The nucleotide sequence and amino acid sequence translated therefrom are as followings (wherein, the underlined sequence is magainin 1 or magainin 2):

```
Prepromagainin
ccaaaggcctctgcggatgaagatatggatgaaagagaggtccggggaattggt (SEQ ID NO:15)
 P   K   A   S   A   D   E   D   M   D   E   R   E   V   R  G   I   G  (SEQ ID NO:16)

aaattttgcattcagcgggcaaatttggaaaagcttttgtgggagagataatg
 K   F   L   H   S   A   G   K   F   G   K   A   F   V   G   E   I   M aagtcaaaacgagatgcagaagcagtaggaccagaggcctttgcagatgaagat
 K   S   K   R   D   A   E   A   V   G   P   E   A   F   A   D   E   D ttagatgaaagagaggtccggggaattggtaaattttgcactcagcaaaaaaa
 L   D   E   R   E   V   R   G   I   G   K   F   L   H   S   A   K   K tttggaaaagcttttgtgggagagataatgaattcaaaacgagatgcagaagca
 F   G   K   A   F   V   G   E   I   M   N   S   K   R   D   A   E   A gtaggaccagaggcctttgcagatgaagatttagatgaaagagaggtccgggga
 V   G   P   E   A   F   A   D   E   D   L   D   E   R   E   V   R   G attggtaaattttgcactcagcaaaaaaatttggaaaagcttttgtgggagaa
 I   G   K   F   L   H   S   A   K   K   F   G   K   A   F   V   G   E ataatgaattcaaaacgagatgcagaagcagtaggaccagaggcctttgcagat
 I   M   N   S   K   R   D   A   E   A   V   G   P   E   A   F   A   D gaagatttagatgaaagagaggtccggggaattggtaaattttgcactcagca
 E   D   L   D   E   R   E   V   R   G   I   G   K   F   L   H   S   A aaaaaatttggaaaagcttttgtgggagaaataatgaattcaaaacgagatgca
 K   K   F   G   K   A   F   V   G   E   I   M   N   S   K   R   D   A gaagcagtaggaccagaggcctttgcagatgaagatttagatgaaagagaggtc
 E   A   V   G   P   E   A   F   A   D   E   D   L   D   E   R   E   V cggggaattggtaaattttgcactcagcaaaaaaatttggaaaagcttttgtg
 R   G   I   G   K   F   L   H   S   A   K   K   F   G   K   A   F   V ggagagataatgaattcaaaacgagatgcagaagcagtaggaccagaggccttt
 G   E   I   M   N   S   K   R   D   A   E   A   V   G   P   E   A   F gcagatgaagatttagatgaaagagaggtccggggaattggtaaattttgcac
 A   D   E   D   L   D   E   R   E   V   R   G   I   G   K   F   L   H tcagcaaaaaaatttggaaaagcttttgtgggagagataatgaattcaaaacga
 S   A   K   K   F   G   K   A   F   V   G   E   I   M   N   S   K   R gatgcagaagcagta
 D   A   E   A   V
```

Figure 5B:
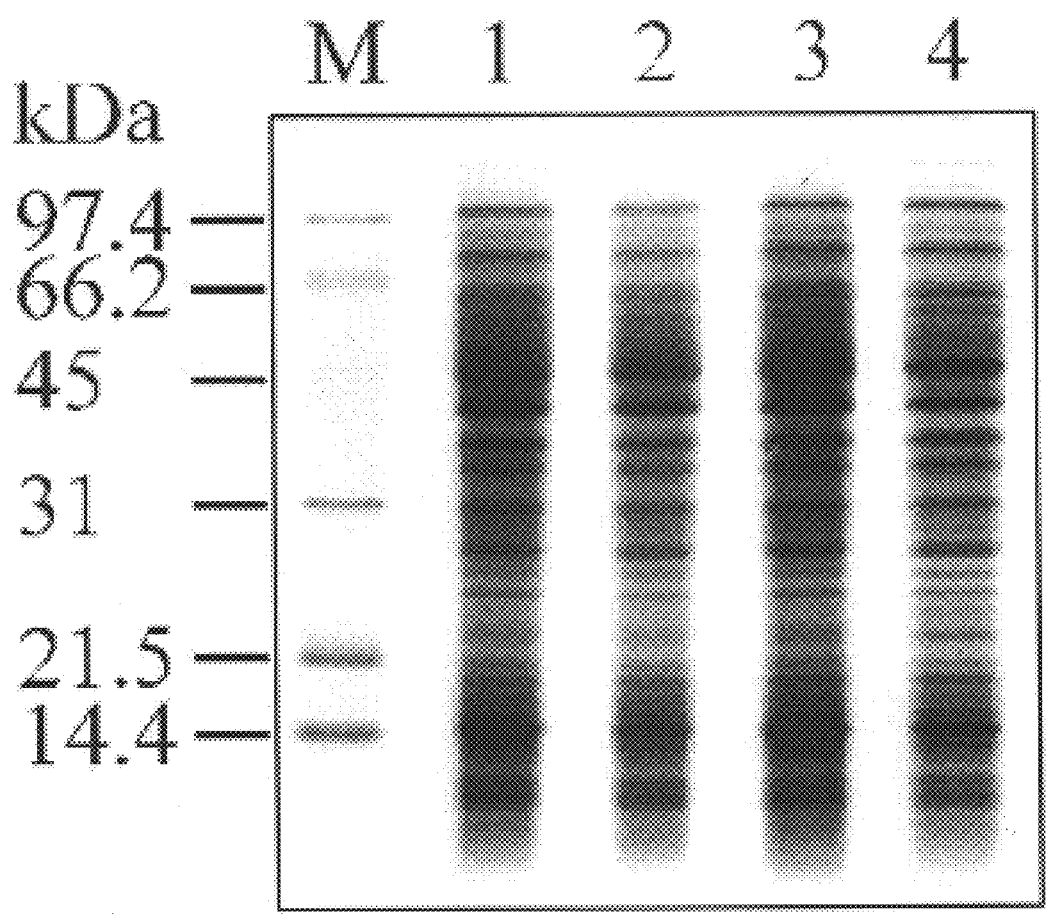
FIG. 5(B) is SDS-PAGE pattern of cell lysates of *E. coli* transformed with vectors containing prepromagainin gene after induction of protein expression.

The cultured transformants were harvested and lysed. The lysates thus obtained were analyzed by the aid of SDS-PAGE (see: FIG. 5(B)). In FIG. 5(B), lane M shows molecular weight markers (97.4, 66.2, 45, 31, 21.5, 14.4 Kd); lanes 1 and 2 show cell lysates of *E. coli* transformed with pET21b before and after IPTG induction; lanes 3 and 4 show cell lysate of *E. coli* transformed with pET21b-(prepromagainin) before and after IPTG induction. As shown in FIG. 5(B), it was found that expression of prepromagainin was not observed when the prepromagainin without cysteine residue was expressed using the same expression system.

Comparative Example 2

A fusion gene was constructed with glutathione-S-transferase (GST) sequence and prepro defensin sequence from HNP-I as an acidic peptide gene, and PGQ, as an antimicrobial peptide gene.

Figure 6:
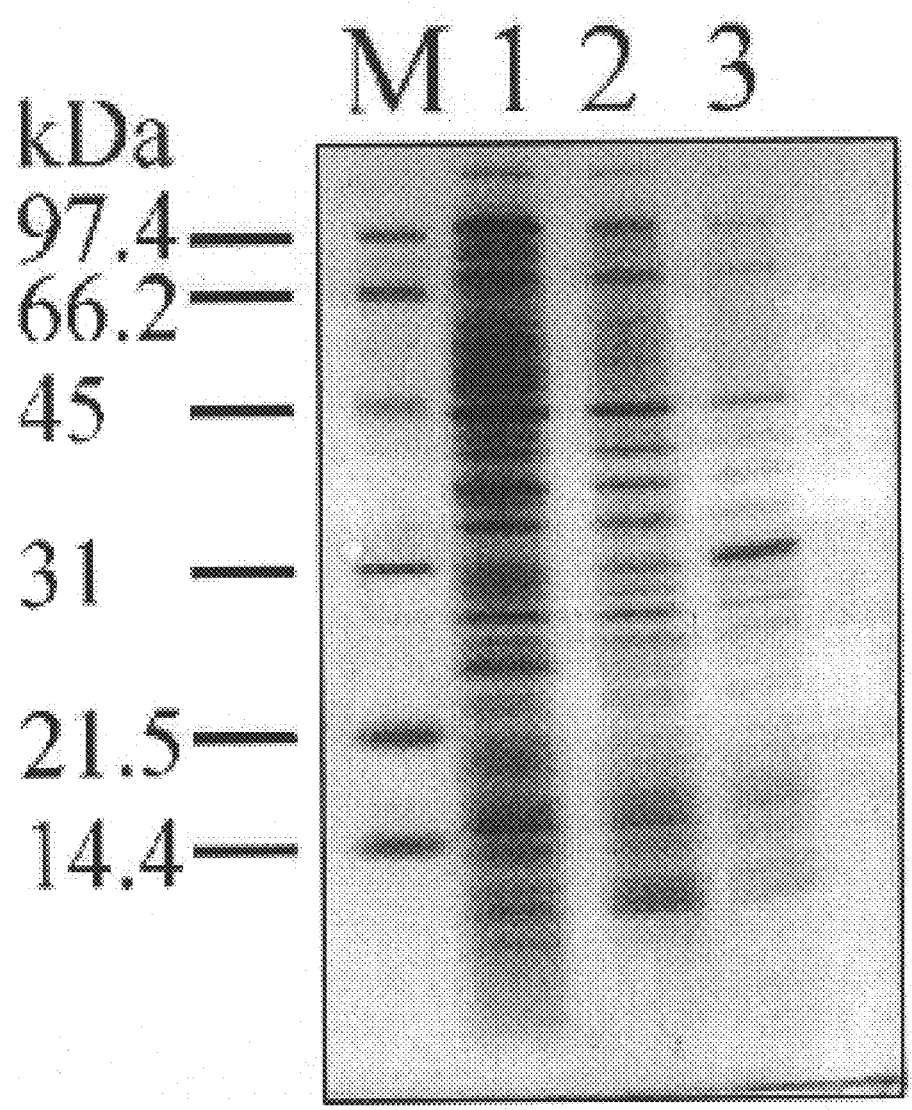
FIG. 6 is SDS-PAGE pattern of cell lysates of *E. coli* transformed with vectors comprising fusion genes containing Guamerin gene and genes of various antimicrobial peptides, after induction of protein expression.

The preprodefensin sequence and the GST gene were treated with BspLU11I and NcoI, respectively, and ligated with PGQ gene digested with NcoI. One methionine residue was incorporated between the acidec peptide and the antimicrobial peptide for further cleavage with CNBr. The obtained fusion genes were cloned into pRSET (Invitrogen, USA) vector and transformed into *E. coli* HMS174(DE3). The expression of the fusion peptides were analyzed by SDS-PAGE (see: FIG. 6). In FIG. 6, lane M shows molecular weight markers (97.4, 66.2, 45, 31, 21.5, 14.4 Kd); lane 1 shows cell lysates of *E. coli* HMS174(DM3); lanes 2 and 3 show cell lysates of *E. coli* harboring the vectors having the fusion genes of prepro definsin-PGQ and GST-PGQ.

Growth of *E.coli* cells harboring the vectors having the above fusion genes was severely inhibited. As shown in FIG. 6, it was found that the expression of fusion peptide was not observed with prepro defensin as acidic peptide, while very low expression was observed with GST as acidic peptide.

EXAMPLE 6

Preparation of a Fusion Gene Comprising a Guamerin Gene as an Acidic Peptide Gene The nucleotide sequence (SEQ ID NO:1) ecoding Guamerin was slightly modified so that its C-terminus can be digested with BspHI, and a methionine codon can be inserted in front of the antimicrobial peptide gene, when the guamerin gene is fused to the antimicrobial peptide gene in order to isolate only a pure antimicrobial peptide by CNBr cleavage of the fusion peptide.

First of all, an N-terminal oligonucleotide containing BamHI and NdeI restriction enzyme sites and a C-terminal oligonucleotide containing BamHI and BspHI restriction enzyme sites were synthesized as followings:

N-terminal oligonucleotide:
5'-CGGGATCCATATGCCCCCGGTCGAC-3' (25mer) (SEQ ID NO:17);

C-terminal oligonucleotide:
5'-CGGGATCCTCATGATACCCGCGCAG-3' (25mer) (SEQ ID NO:18)

PCR was carried out by using the N- and C-terminal oligonucleotide primers thus synthesized and the Guamerin gene (FIG. 1) as template, to synthesize a novel Guamerin gene.

Eight antimicrobial peptides known in the art (see: Peptide Science, Vol. 37, 105–122(1995)) were selected to express them in a form of fusion peptide, whose biochemical characteristics are summarized in Table 1. The following DNA sequences (SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35) were deduced from the respective peptide sequences (SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36) based on the codon usage of *E. coli*, and synthesized for late use.

```
Apidaecin I
ggt aac aac cgt ccg gtt tac atc ccg cag ccg cgt ccg ccg    (SEQ ID NO:19)
 G   N   N   R   P   V   Y   I   P   Q   P   R   P   P     (SEQ ID NO:20)

cac ccg cgt act
 H   P   R   I

Bombinin
ggt atc ggt gcg ctg tct gcg aaa ggt gcg ctg aaa ggt ctg    (SEQ ID NO:21)
 G   I   G   A   L   S   A   K   G   A   L   K   G   L     (SEQ ID NO:22)

gcg aaa ggt ctg gcg gaa cac ttc gcg aac
 A   K   G   L   A   E   H   F   A   N

Cercropin A
aaa tgg aaa ttc aaa aaa atc gaa aaa gtt ggt cag aac atc    (SEQ ID NO:23)
 K   W   K   F   K   K   I   E   K   V   G   Q   N   I     (SEQ ID NO:24)

cgt gac ggt atc atc aaa gcg ggt ccg gcg gtt gcg gtt gtt
 R   D   G   I   I   K   A   G   P   A   V   A   V   V ggt cag gcg acc cag atc gcg aaa
 G   Q   A   T   Q   I   A   K Drosocin
ggt aaa ccg cgt ccg tac tct ccg cgt ccg acc tct cac ccg    (SEQ ID NO:25)
 G   K   P   R   P   Y   S   P   R   P   T   S   H   P     (SEQ ID NO:26)

cgt ccg atc gcg gtt
 R   P   I   A   V
```

-continued

HNP-I
gcg tgc tac tgc cgt atc ccg gcg tgc atc gcg ggt gag cgt (SEQ ID NO:27)
 A   C   Y   C   R   I   P   A   C   I   A   G   E   R  (SEQ ID NO:28)

cgt tac ggt acc tgc atc tac cag ggt cgt ctg tgg gcg ttc
 R   Y   G   T   C   I   Y   Q   G   R   L   W   A   F tgc tgc
 C   C Indolicidin
atc ctg ccg tgg aaa tgg ccg tgg tgg ccg tgg cgt cgt (SEQ ID NO:29)
 I   L   P   W   K   W   P   W   W   P   W   R   R  (SEQ ID NO:30)

Magainin(MSI-344)
ggt atc ggc aaa ttc ctg aaa aag gct aag aaa ttt ggt aag (SEQ ID NO:31)
 G   I   G   K   F   L   K   K   A   K   K   F   G   K  (SEQ ID NO:32)

gcg ttc gtt aaa atc ctg aaa aag
 A   F   V   K   I   L   K   K

Melittin
ggt act ggt gcg gtt ctg aaa gtt ctg acc acc ggt ctg ccg (SEQ ID NO:33)
 G   I   G   A   V   L   K   V   L   T   T   G   L   P  (SEQ ID NO:34)

gcg ctg atc tct tgg atc aaa cgt aaa cgt cag cag
 A   L   I   S   W   I   K   R   K   R   Q   Q Tachyplesin I
aaa tgg tgc ttc cgt gtt tgc tac cgt ggt atc tgc tac cgt (SEQ ID NO:35)
 K   W   C   F   F   V   C   Y   R   G   I   C   Y   R  (SEQ ID NO:36)

cgt tgc cgt
 R   C   R

TABLE 1

Biochemical characteristics of various antimicrobial peptides*

| Peptides | Number of amino acid | Molecular weight (kDa) | pI | Origin |
|---|---|---|---|---|
| Apidaecin I | 18 | 2.1 | 12.21 | Insect |
| Bombinin | 24 | 29 | 10.34 | Frog |
| Ceropin A | 36 | 3.89 | 10.89 | Moth |
| Drosocin | 19 | 2.11 | 12.22 | Fly |
| HNP1 | 30 | 3.46 | 8.28 | Human |
| Indolicidin | 13 | 1.91 | 12.51 | Cow |
| Magainin (MSI-344) | 22 | 2.48 | 11.41 | Frog |
| Melittin | 26 | 2.85 | 12.53 | Insect |
| Tachyplesin I | 17 | 2.27 | 10.01 | Crab |

*Excerpted from Peptide Science, Vol 37, 105–122 (1995)

Various Guamerin-antimicrobial peptide fusion genes were prepared by fusing the synthesized Guamerin gene with various antimicrobial peptide genes shown in Table 1, respectively. That is, the synthesized Guamerin gene was digested with BspHI to give the termini complementary to BspHI or NcoI cleavage site, and fused with the antimicrobial peptide genes synthesized which were digested with NcoI to prepare fusion genes.

EXAMPLE 7

Expression of Antimicrobial Peptide

In order to express the fusion genes prepared in Example 6 in *E. coli*, PRSET (Invitrogen, USA) expression vector was employed. The expression vector was digested with BamHI and EcoRI, dephosphorylated, and Guamerin-antimicrobial peptide fusion genes synthesized in Example 6 were cloned. *E. coli* BL21(DE3) pLysS was transformed with the vectors having fusion genes by CaCl$_2$ method (see: Sambrook et al., Molecular Cloning: *A Laboratory Manual*, 2nd ed. (1989)).

Figure 7:
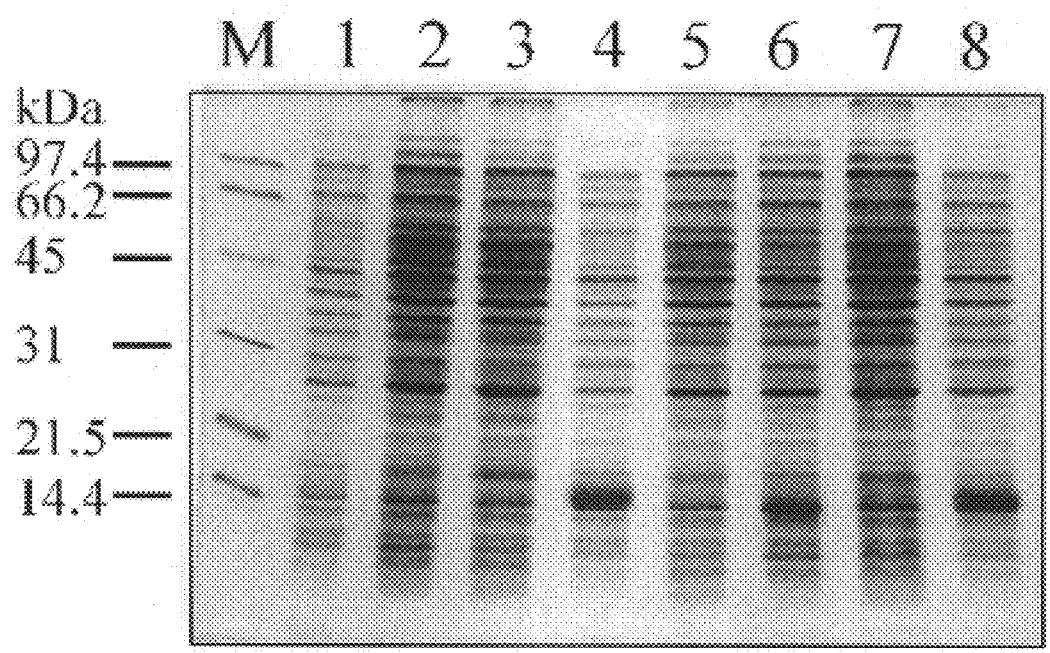
FIG. 7 is SDS-PAGE pattern of cell lysates of *E. coli* transformed with vectors comprising fusion genes containing Guamerin gene and genes of various antimicrobial peptides, after induction of protein expression.

The transformants were cultured in 5 ml of LB medium supplemented with ampicillin at 37° C. overnight. The cultured cells were diluted in 5 ml of fresh LB medium in a final concentration of 1%(v/v), and incubated at 37° C. for 2 hours. Then, lactose was added to the cultured medium in a final concentration of 2% to induce the expression of the fusion peptides at 37° C. for 4 hours. The expression of fusion genes was analyzed by SDS-PAGE (see: FIG. 7). In FIG. 7, lane M shows molecular weight markers (97.4, 66.2, 45, 31, 21.5, 14.4 Kd); lanes 1–8 show cell lysates of *E. coli* transformed with fusion genes in which genes encoding apidaecin I, bombinin, cecropin A, drosocin, HNP1, indolicidin, melittin and tachyplesin I were employed as antimictobial peptide genes, respectively.

As clearly illustrated and demonstrated as above, the present invention provides a method for mass production of antimicrobial peptide, which comprises a step of preparing the antimicrobial peptide as a fusion peptide with a foreign peptide. In accordance with the present invention, the inhibitory effect of the expressed antimicrobial peptide on the growth of host microorganism can be dramatically minimized by fusing it with the acidic peptide. Accordingly, antimicrobial peptides can be produced massively from a recombinant microorganism regardless of the kind of the antimicrobial peptides.

What is claimed is:

1. A method for mass production of antimicrobial peptide, which comprises the steps of:
   (i) constructing a fusion gene containing a first gene encoding a negatively charged acidic peptide having at least two cysteine residues and a second gene encoding a positively charged basic antimicrobial peptide;
   (ii) inserting the fusion gene into an expression vector, wherein the promoter of the expression vector is operatively linked to the fusion gene;
   (iii) transforming a host microogranism with an expression vector comprising the fusion gene;
   (iv) cultivating the transformed microogranism to express a fusion peptide containing the acidic peptide and the antimicrobial peptide; and,
   (v) recovering the expressed antimicrobial peptide.

2. The method of claim 1, wherein the fusion gene contains at least one cleavage site for a protease or a chemical between the acidic peptide and the antimicrobial peptide.

3. The method of claim 1, wherein the negative charges of the acidic peptide neutralizes the positive charges of the antimicrobial peptide.

4. The method of claim 1, wherein the expression vector comprises a multimer of the fusion gene.

5. The method of claim 1, wherein the gene is a multimeric form of a first gene encoding an acidic peptide and a second gene encoding a positively charged antimicrobial peptide, which is fused to the first gene.

* * * * *

SEQUENCE LISTING

<160> NUMBER OF SEQ ID NOS: 36

<210> SEQ ID NO 1
<211> LENGTH: 183
<212> TYPE: DNA
<213> ORGANISM: Unknown
<220> FEATURE:
<223> OTHER INFORMATION: Guamerin gene

<400> SEQUENCE: 1 ccccggtcg acgagaatgc ggaggacaca catggtctct gcggggaaaa aacctgctct    60
ccagcacaag tctgtctaaa caacgaatgc gtttgcactg caatcagatg cgagatcttc   120
tgtcctaacg gattcaaagt tgatgagaat ggatgcgaat acccatgtac ctgcgcgggg   180
atc                                                                 183

<210> SEQ ID NO 2
<211> LENGTH: 61
<212> TYPE: PRT
<213> ORGANISM: Unknown
<220> FEATURE:
<223> OTHER INFORMATION: Guamerin

<400> SEQUENCE: 2

Pro Pro Val Asp Glu Asn Ala Glu Asp Thr His Gly Leu Cys Gly Glu
 1               5                  10                  15

Lys Thr Cys Ser Pro Ala Gln Val Cys Leu Asn Asn Glu Cys Val Cys
            20                  25                  30

Thr Ala Ile Arg Cys Glu Ile Phe Cys Pro Asn Gly Phe Lys Val Asp
        35                  40                  45

Glu Asn Gly Cys Glu Tyr Pro Cys Thr Cys Ala Gly Ile
    50                  55                  60

<210> SEQ ID NO 3
<211> LENGTH: 81
<212> TYPE: DNA
<213> ORGANISM: Unknown
<220> FEATURE:
<223> OTHER INFORMATION: MIS (magainin intervening segment) gene

<400> SEQUENCE: 3
cccctgtgcg atgcagaagc agtaggacca gaggcctttg cagatgaaga tttagatgaa    60 tgccccggg tcttctagag t                                               81

<210> SEQ ID NO 4
<211> LENGTH: 27
<212> TYPE: PRT
<213> ORGANISM: Unknown
<220> FEATURE:
<223> OTHER INFORMATION: MIS (magainin intervening segment)

<400> SEQUENCE: 4

Pro Leu Cys Asp Ala Glu Ala Val Gly Pro Glu Ala Phe Ala Asp Glu
 1               5                  10                  15

Asp Leu Phe Ala Asp Glu Asp Leu Asp Glu Cys
            20                  25

<210> SEQ ID NO 5
<211> LENGTH: 84
<212> TYPE: PRT
<213> ORGANISM: Artificial Sequence

```
<220> FEATURE:
<223> OTHER INFORMATION: Guamerin/BuforinII fusion protein

<400> SEQUENCE: 5

Pro Pro Val Asp Glu Asn Ala Lys Asp Thr His Gly Leu Cys Gly Glu
 1               5                  10                  15

Lys Thr Cys Ser Pro Ala Gln Val Cys Leu Asn Asn Glu Cys Val Cys
                20                  25                  30

Thr Ala Ile Arg Cys Met Ile Phe Cys Pro Asn Gly Phe Lys Val Asp
            35                  40                  45

Lys Asn Gly Cys Glu Tyr Pro Cys Thr Cys Ala Gly Ile Met Thr Arg
    50                  55                  60

Ser Ser Arg Ala Gly Leu Gln Phe Pro Val Gly Arg Val His Arg Leu
65                  70                  75                  80

Leu Arg Lys Met

<210> SEQ ID NO 6
<211> LENGTH: 46
<212> TYPE: PRT
<213> ORGANISM: Artificial Sequence
<220> FEATURE:
<223> OTHER INFORMATION: MIS (magainin intervening segment)/BuforinII
      fusion protein

<400> SEQUENCE: 6

Pro Leu Cys Asp Ala Lys Ala Val Gly Pro Glu Ala Phe Ala Asp Glu
 1               5                  10                  15

Asp Leu Asp Glu Cys Pro Leu Met Thr Arg Ser Ser Arg Ala Gly Leu
                20                  25                  30

Gln Phe Pro Val Gly Arg Val His Arg Leu Leu Arg Lys Met
            35                  40                  45

<210> SEQ ID NO 7
<211> LENGTH: 84
<212> TYPE: PRT
<213> ORGANISM: Artificial Sequence
<220> FEATURE:
<223> OTHER INFORMATION: Guamerin/MSI-78 fusion protein

<400> SEQUENCE: 7

Pro Pro Val Asp Glu Asn Ala Glu Asp Thr His Gly Leu Cys Gly Glu
 1               5                  10                  15

Lys Thr Cys Ser Pro Ala Gln Val Cys Leu Asn Asn Glu Cys Val Cys
                20                  25                  30

Thr Ala Ile Arg Cys Glu Ile Phe Cys Pro Asn Gly Phe Lys Val Asp
            35                  40                  45

Glu Asn Gly Cys Glu Tyr Pro Cys Thr Cys Ala Gly Ile Cys Gly Ile
    50                  55                  60

Gly Lys Phe Leu Lys Lys Ala Lys Lys Phe Gly Lys Ala Phe Val Lys
65                  70                  75                  80

Ile Leu Lys Lys

<210> SEQ ID NO 8
<211> LENGTH: 84
<212> TYPE: PRT
<213> ORGANISM: Artificial Sequence
<220> FEATURE:
<223> OTHER INFORMATION: Guamerin/MSI-78 fusion protein

<400> SEQUENCE: 8
```

-continued

Pro Pro Val Asp Glu Asn Ala Glu Asp Thr His Gly Leu Cys Gly Glu
1               5                   10                  15

Lys Thr Cys Ser Pro Ala Gln Val Cys Leu Asn Asn Glu Cys Val Cys
                20                  25                  30

Thr Ala Ile Arg Cys Glu Ile Phe Cys Pro Asn Gly Phe Lys Val Asp
            35                  40                  45

Glu Asn Gly Cys Glu Tyr Pro Cys Thr Cys Ala Gly Ile Met Gly Ile
    50                  55                  60

Gly Lys Phe Leu Lys Lys Ala Lys Lys Phe Gly Lys Ala Phe Val Lys
65              70                  75                  80

Ile Leu Lys Lys

<210> SEQ ID NO 9
<211> LENGTH: 21
<212> TYPE: PRT
<213> ORGANISM: Artificial Sequence
<220> FEATURE:
<223> OTHER INFORMATION: Buforin II

<400> SEQUENCE: 9

Thr Arg Ser Ser Arg Ala Gly Leu Gln Phe Pro Val Gly Arg Val His
1               5                   10                  15

Arg Leu Leu Arg Lys
            20

<210> SEQ ID NO 10
<211> LENGTH: 32
<212> TYPE: DNA
<213> ORGANISM: Unknown
<220> FEATURE:
<223> OTHER INFORMATION: Guamerin gene 5' PCR primer

<400> SEQUENCE: 10
aaagaagacg gcccccggtc gacgagaatg cg          32

<210> SEQ ID NO 11
<211> LENGTH: 30
<212> TYPE: DNA
<213> ORGANISM: Unknown
<220> FEATURE:
<223> OTHER INFORMATION: Guamerin gene 3' PCR primer

<400> SEQUENCE: 11
gctgctacgg gtcatgatcc ccgcgcaggt          30

<210> SEQ ID NO 12
<211> LENGTH: 30
<212> TYPE: DNA
<213> ORGANISM: Artificial Sequence
<220> FEATURE:
<223> OTHER INFORMATION: BuforinII gene 5' PCR primer

<400> SEQUENCE: 12
acctgcgcgg ggatcatgac ccgtagcagc          30

<210> SEQ ID NO 13
<211> LENGTH: 18
<212> TYPE: DNA
<213> ORGANISM: Artificial Sequence
<220> FEATURE:
<223> OTHER INFORMATION: BuforinII gene 3' PCR primer

<400> SEQUENCE: 13

-continued tgcatgcctg caggtcga                                               18

<210> SEQ ID NO 14
<211> LENGTH: 22
<212> TYPE: PRT
<213> ORGANISM: Artificial Sequence
<220> FEATURE:
<223> OTHER INFORMATION: MSI-78

<400> SEQUENCE: 14

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 15
<211> LENGTH: 825
<212> TYPE: DNA
<213> ORGANISM: Unknown
<220> FEATURE:
<223> OTHER INFORMATION: Prepromagainin gene

<400> SEQUENCE: 15
ccaaaggcct ctgcggatga agatatggat gaaagagagg tccggggaat tggtaaattt      60
ttgcattcag cgggcaaatt tggaaaagct tttgtgggag ataatgaa gtcaaaacga      120
gatgcagaag cagtaggacc agaggccttt gcagatgaag atttagatga agagaggtc     180
cggggaattg gtaaattttt gcactcagca aaaaatttg gaaaagcttt tgtgggagag    240
ataatgaatt caaaacgaga tgcagaagca gtaggaccag aggcctttgc agatgaagat   300
ttagatgaaa gagaggtccg gggaattggt aaattttgc actcagcaaa aaatttgga     360
aaagcttttg tgggagaaat aatgaattca aaacgagatg cagaagcagt aggaccagag   420
gcctttgcag atgaagattt agatgaaaga gaggtccggg gaattggtaa attttgcac    480
tcagcaaaaa aatttggaaa agcttttgtg ggagaaataa tgaattcaaa acgagatgca   540
gaagcagtag gaccagaggc ctttgcagat gaagatttag atgaaagaga ggtccgggga   600
attggtaaat ttttgcactc agcaaaaaaa tttggaaaag cttttgtggg agagataatg   660
aattcaaaac gagatgcaga agcagtagga ccagaggcct tgcagatga agattagat   720
gaaagagagg tccggggaat tggtaaattt ttgcactcag caaaaaaatt tggaaaagct   780
tttgtgggag ataatgaa ttcaaaacga gatgcagaag cagta                   825

<210> SEQ ID NO 16
<211> LENGTH: 275
<212> TYPE: PRT
<213> ORGANISM: Unknown
<220> FEATURE:
<223> OTHER INFORMATION: Prepromagainin

<400> SEQUENCE: 16

Pro Lys Ala Ser Ala Asp Glu Asp Met Asp Glu Arg Glu Val Arg Gly
1               5                   10                  15

Ile Gly Lys Phe Leu His Ser Ala Gly Lys Phe Gly Lys Ala Phe Val
            20                  25                  30

Gly Glu Ile Met Lys Ser Lys Arg Asp Ala Glu Ala Val Gly Pro Glu
        35                  40                  45

Ala Phe Ala Asp Glu Asp Leu Asp Glu Arg Glu Val Arg Gly Ile Gly
    50                  55                  60

Lys Phe Leu His Ser Ala Lys Lys Phe Gly Lys Ala Phe Val Gly Glu

-continued

```
            65                  70                  75                  80
Ile Met Asn Ser Lys Arg Asp Ala Glu Ala Val Gly Pro Glu Ala Phe
                        85                  90                  95

Ala Asp Glu Asp Leu Asp Glu Arg Glu Val Arg Gly Ile Gly Lys Phe
            100                 105                 110

Leu His Ser Ala Lys Lys Phe Gly Lys Ala Phe Val Gly Glu Ile Met
        115                 120                 125

Asn Ser Lys Arg Asp Ala Glu Ala Val Gly Pro Glu Ala Phe Ala Asp
    130                 135                 140

Glu Asp Leu Asp Glu Arg Glu Val Arg Gly Ile Gly Lys Phe Leu His
145                 150                 155                 160

Ser Ala Lys Lys Phe Gly Lys Ala Phe Val Gly Glu Ile Met Asn Ser
                165                 170                 175

Lys Arg Asp Ala Glu Ala Val Gly Pro Glu Ala Phe Ala Asp Glu Asp
            180                 185                 190

Leu Asp Glu Arg Glu Val Arg Gly Ile Gly Lys Phe Leu His Ser Ala
        195                 200                 205

Lys Lys Phe Gly Lys Ala Phe Val Gly Glu Ile Met Asn Ser Lys Arg
    210                 215                 220

Asp Ala Glu Ala Val Gly Pro Glu Ala Phe Ala Asp Glu Asp Leu Asp
225                 230                 235                 240

Glu Arg Glu Val Arg Gly Ile Gly Lys Phe Leu His Ser Ala Lys Lys
                245                 250                 255

Phe Gly Lys Ala Phe Val Gly Glu Ile Met Asn Ser Lys Arg Asp Ala
            260                 265                 270

Glu Ala Val
        275

<210> SEQ ID NO 17
<211> LENGTH: 25
<212> TYPE: DNA
<213> ORGANISM: Artificial Sequence
<220> FEATURE:
<223> OTHER INFORMATION: N-terminal oligonucleotide derived from
      Guamerin gene and containing BamHI and NdeI restriction
      sites

<400> SEQUENCE: 17
cgggatccat atgccccccgg tcgac                                    25

<210> SEQ ID NO 18
<211> LENGTH: 25
<212> TYPE: DNA
<213> ORGANISM: Artificial Sequence
<220> FEATURE:
<223> OTHER INFORMATION: C-terminal oligonucleotide derived from
      Guamerin gene and containing BamHI and BspHI restriction
      sites

<400> SEQUENCE: 18
cgggatcctc atgatacccg cgcag                                     25

<210> SEQ ID NO 19
<211> LENGTH: 54
<212> TYPE: DNA
<213> ORGANISM: Artificial Sequence
<220> FEATURE:
<223> OTHER INFORMATION: DNA sequence deduced from Apidaecin I peptide
      sequence based on the codon usage of E.coli

<400> SEQUENCE: 19
```

```
ggtaacaacc gtccggttta catcccgcag ccgcgtccgc cgcacccgcg tact           54
```

<210> SEQ ID NO 20
<211> LENGTH: 18
<212> TYPE: PRT
<213> ORGANISM: Unknown
<220> FEATURE:
<223> OTHER INFORMATION: Apidaecin I

<400> SEQUENCE: 20

Gly Asn Asn Arg Pro Val Tyr Ile Pro Gln Pro Arg Pro Pro His Pro
 1               5                  10                  15

Arg Ile

<210> SEQ ID NO 21
<211> LENGTH: 72
<212> TYPE: DNA
<213> ORGANISM: Artificial Sequence
<220> FEATURE:
<223> OTHER INFORMATION: DNA sequence deduced from Bombinin peptide
      sequence based on codon usage of E. coli

<400> SEQUENCE: 21

```
ggtatcggtg cgctgtctgc gaaaggtgcg ctgaaaggtc tggcgaaagg tctggcggaa    60
cacttcgcga ac                                                        72
```

<210> SEQ ID NO 22
<211> LENGTH: 24
<212> TYPE: PRT
<213> ORGANISM: Unknown
<220> FEATURE:
<223> OTHER INFORMATION: Bombinin

<400> SEQUENCE: 22

Gly Ile Gly Ala Leu Ser Ala Lys Gly Ala Leu Lys Gly Leu Ala Lys
 1               5                  10                  15

Gly Leu Ala Glu His Phe Ala Asn
            20

<210> SEQ ID NO 23
<211> LENGTH: 108
<212> TYPE: DNA
<213> ORGANISM: Artificial Sequence
<220> FEATURE:
<223> OTHER INFORMATION: DNA sequence deduced from Cecropin A peptide
      sequence based on codon usage of E. coli

<400> SEQUENCE: 23

```
aaatggaaat tcaaaaaaat cgaaaaagtt ggtcagaaca tccgtgacgg tatcatcaaa    60
gcgggtccgg cggttgcggt tgttggtcag gcgacccaga tcgcgaaa               108
```

<210> SEQ ID NO 24
<211> LENGTH: 36
<212> TYPE: PRT
<213> ORGANISM: Unknown
<220> FEATURE:
<223> OTHER INFORMATION: Cecropin A

<400> SEQUENCE: 24

Lys Trp Lys Phe Lys Lys Ile Glu Lys Val Gly Gln Asn Ile Arg Asp
 1               5                  10                  15

Gly Ile Ile Lys Ala Gly Pro Ala Val Ala Val Val Gly Gln Ala Thr
            20                  25                  30

Gln Ile Ala Lys
        35

<210> SEQ ID NO 25
<211> LENGTH: 57
<212> TYPE: DNA
<213> ORGANISM: Artificial Sequence
<220> FEATURE:
<223> OTHER INFORMATION: DNA sequence deduced from Drosocin peptide
      sequence based on codon usage of E. coli

<400> SEQUENCE: 25
ggtaaaccgc gtccgtactc tccgcgtccg acctctcacc cgcgtccgat cgcggtt          57

<210> SEQ ID NO 26
<211> LENGTH: 19
<212> TYPE: PRT
<213> ORGANISM: Unknown
<220> FEATURE:
<223> OTHER INFORMATION: Drosocin

<400> SEQUENCE: 26

Gly Lys Pro Arg Pro Tyr Ser Pro Arg Pro Thr Ser His Pro Arg Pro
 1               5                  10                  15

Ile Ala Val

<210> SEQ ID NO 27
<211> LENGTH: 90
<212> TYPE: DNA
<213> ORGANISM: Artificial Sequence
<220> FEATURE:
<223> OTHER INFORMATION: DNA sequence deduced from HNP-I peptide
      sequence based on codon usage of E. coli

<400> SEQUENCE: 27
gcgtgctact gccgtatccc ggcgtgcatc gcgggtgagc gtcgttacgg tacctgcatc       60
taccagggtc gtctgtgggc gttctgctgc                                        90

<210> SEQ ID NO 28
<211> LENGTH: 30
<212> TYPE: PRT
<213> ORGANISM: Homo sapiens

<400> SEQUENCE: 28

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30

<210> SEQ ID NO 29
<211> LENGTH: 39
<212> TYPE: DNA
<213> ORGANISM: Artificial Sequence
<220> FEATURE:
<223> OTHER INFORMATION: DNA sequence deduced from Indolicidin peptide
      sequence based on codon usage of E. coli

<400> SEQUENCE: 29
atcctgccgt ggaaatggcc gtggtggccg tggcgtcgt                              39

<210> SEQ ID NO 30
<211> LENGTH: 13
<212> TYPE: PRT
<213> ORGANISM: Bos taurus

<400> SEQUENCE: 30

Ile Leu Pro Trp Lys Trp Pro Trp Trp Pro Trp Arg Arg
1               5                   10

<210> SEQ ID NO 31
<211> LENGTH: 66
<212> TYPE: DNA
<213> ORGANISM: Artificial Sequence
<220> FEATURE:
<223> OTHER INFORMATION: DNA sequence deduced from Megainin (MSI-344)
      peptide sequence based on codon usage of E. coli

<400> SEQUENCE: 31

```
ggtatcggca aattcctgaa aaaggctaag aaatttggta aggcgttcgt taaaatcctg    60
aaaaag                                                                66
```

<210> SEQ ID NO 32
<211> LENGTH: 22
<212> TYPE: PRT
<213> ORGANISM: Unknown
<220> FEATURE:
<223> OTHER INFORMATION: Magainin (MSI-344)

<400> SEQUENCE: 32

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 33
<211> LENGTH: 78
<212> TYPE: DNA
<213> ORGANISM: Artificial Sequence
<220> FEATURE:
<223> OTHER INFORMATION: DNA sequence deduced from Melittin peptide
      sequence based on codon usage of E. coli

<400> SEQUENCE: 33

```
ggtactggtg cggttctgaa agttctgacc accggtctgc cggcgctgat ctcttggatc    60
aaacgtaaac gtcagcag                                                   78
```

<210> SEQ ID NO 34
<211> LENGTH: 26
<212> TYPE: PRT
<213> ORGANISM: Unknown
<220> FEATURE:
<223> OTHER INFORMATION: Melittin

<400> SEQUENCE: 34

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 35
<211> LENGTH: 51
<212> TYPE: DNA
<213> ORGANISM: Artificial Sequence
<220> FEATURE:
<223> OTHER INFORMATION: DNA sequence deduced from Tachyplesin I peptide
      sequence based on codon usage of E. coli

<400> SEQUENCE: 35

```
aaatggtgct tccgtgtttg ctaccgtggt atctgctacc gtcgttgccg t                51
```

<210> SEQ ID NO 36
<211> LENGTH: 17
<212> TYPE: PRT
<213> ORGANISM: Unknown
<220> FEATURE:
<223> OTHER INFORMATION: Tachyplesin I

<400> SEQUENCE: 36

```
Lys Trp Cys Phe Phe Val Cys Tyr Arg Gly Ile Cys Tyr Arg Arg Cys
 1               5                  10                  15

Arg
```